United States Patent [19]

Fukazawa et al.

[11] Patent Number: 5,434,155
[45] Date of Patent: Jul. 18, 1995

[54] QUINOLINE DERIVATIVE FUMARATES

[75] Inventors: Nobuyuki Fukazawa; Tuneji Suzuki; Kengo Otsuka; Osamu Yano; Daiji Iwata; Yukichi Kawai, all of Mobara, Japan

[73] Assignee: Mitsui Toatsu Chemicals, Incorporated, Tokyo, Japan

[21] Appl. No.: 76,589

[22] Filed: Jun. 15, 1993

[30] Foreign Application Priority Data

Jun. 18, 1992 [JP] Japan .................. 4-159318

[51] Int. Cl.$^6$ .................. A61K 31/495; C07D 401/00
[52] U.S. Cl. ..................... 514/253; 544/363
[58] Field of Search ............. 544/363; 514/253

[56] References Cited

U.S. PATENT DOCUMENTS

| 4,965,271 | 10/1990 | Mandell et al. | 514/263 |
| 5,039,666 | 8/1991 | Novick, Jr. | 514/39 |
| 5,204,348 | 4/1993 | Fukazawa et al. | 514/253 |

FOREIGN PATENT DOCUMENTS 0363212 4/1990 European Pat. Off. .

OTHER PUBLICATIONS

Journal of Medicinal Chemistry, vol. 35, No. 13, Jun. 26, 1992, pp. 2481–2496, A. Dhainaut, et al., "New Triazine Derivatives as Potent Modulators of Multidrug Resistance".

Primary Examiner—Cecilia Tsang
Attorney, Agent, or Firm—Oblon, Spivak, McClelland, Maier & Neustadt

[57] ABSTRACT

Compounds having an activity to stimulate the carcinostatic effect of carcinostatic agents, which can be expressed by the following general formula (1):

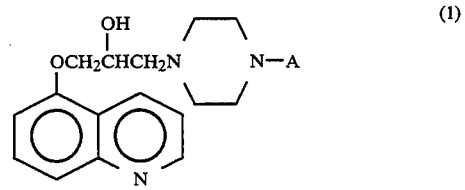

in which A is

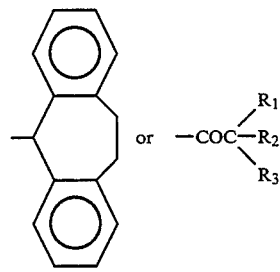

(in which $R_1$, $R_2$ and $R_3$ are each independent and represent a hydrogen atom or a phenyl group) are made into fumarates so as to improve their oral absorbability and solubility in water without interfering with their effects.

5 Claims, No Drawings

QUINOLINE DERIVATIVE FUMARATES

BACKGROUND OF THE INVENTION

1. Field of the Invention

The present invention relates to quinoline derivative fumarates having a stimulating activity on the carcinostatic effect. The present invention further relates to agents containing said fumarates which stimulate the carcinostatic effect of carcinostatic agents and to a method of stimulating the carcinostatic effect using said carcinostatic agents in combination. 2. Description of the related Art The number of cancer patients worldwide has been increasing every year; in Japan, cancer has the highest mortality rate of all the cause of death, and social interest in cancer treatment, particularly in chemotherapy, is high. However, to date, an extremely small number of effective drugs has been developed for cancer treatment although extensive efforts have been made.

One of the greatest clinical problems with chemotherapy for cancer treatment is that cancer cells become resistant to various kinds of carcinostatic agents. That is, for example, cells which are resistant to adriamycin are resistant also to a number of other carcinostatic agents, which makes cancer treatment very difficult. This multi-drug resistance phenomenon is considered to be caused by a protein called glycoprotein P, which is expressed by cancer cells on the surface of the cells and stimulates extracellular excretion of carcinostatic agents.

Accordingly, it has been strongly desired to develope an agent having the following characteristics:
  (a) It can interfere with the action of the glycoprotein P and provide a treatment of a cancer having such resistant by overcoming the drug resistance, i.e., it can strongly stimulate carcinostatic effects of caricinostatics.
  (b) It has no or substantially no toxicity for clinical use.

As a result of intensive studies and research under the above-mentioned circumstances, the present inventors found that specific compounds and their salts exhibit a strong action in stimulating carcinostatic effect on drug resistant cancer and have low toxicity and low side effects, which was reported in European Patent Publication No. 0363212 A2. The main compounds them are quinoline derivatives classified in a group of compounds which contain basic amines and are highly fat-soluble. These compounds can be clinically used in practice in a form of an agent for oral administration or for injection; however, these compounds have a disadvantage in oral absorbability or solubility in water because of a limitation in their physical properties. Accordingly, it has been desired to develop a novel compound having improved characteristics of high solubility in water and of sufficient oral absorbability, in which the above-mentioned physical properties are improved.

SUMMARY OF THE INVENTION

As a result of intensive studies to solve the above-mentioned problem, the present inventors found that many active compounds have a basic amine structure. They then tried to improve the physical properties of the compounds by forming salts with several kinds of acids. Among these compounds, fumarates of the quinoline derivatives as a representative active compound, were markedly improved particularly in their physical properties, and have excellent oral absorbability and improved water solubility. Thereby the present invention was completed.

Namely, the quinoline derivative fumarates of the present invention is the salts of the quinoline derivatives represented by the following formula (1) and fumaric acid:

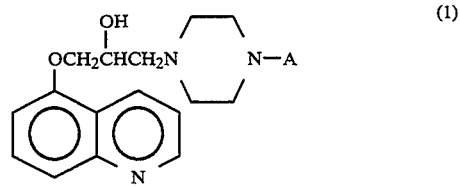

In the formula (1), A represents a group of the following formula (2) or formula (3)

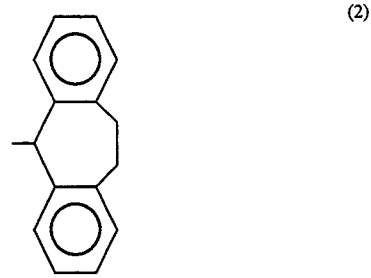

In the formula (3), $R_1$, $R_2$ and $R_3$ represent independently a hydrogen atom or a phenyl group.

The quinoline derivative fumarates of the present invention are excellent in their oral absorbability and have improved solubility in water as will be shown in the Test Examples thereinafter. Accordingly, the present invention is to provide compounds which are extremely beneficial for clinical use as carcinostatic-effect-stimulating agents which are expected to be useful in cancer chemotherapy.

DETAILED DESCRIPTION OF THE PREFERRED EMBODIMENT

In the fumarates of the quinoline derivatives of the formula (1), fumaric acid is used as an acid to compose the salts so that the salts have an excellent oral absorbability and an improved solubility in water.

In order to produce quinoline derivative fumarates of the present invention, conventional methods for the formation of salts of organic amines with organic acids may be used. For example, a free quinoline derivative (which can, for example, be prepared by the method described in European Patent Publication No. 0363212 A2) and free fumaric acid are either separately dissolved in a solvent or mixed together without a solvent and then the salt formed is isolated. Any solvent providing solubilities of the starting materials enough for the reaction can be used without further restriction. As the solvent, water, alcohols such as methanol or ethanol, ordinary organic solvents such as acetone, ethyl acetate or acetonitrile or mixtures of two or more of the solvents can be used. The reaction can be carried out at a temperature between the melting point to boiling point of the solvent used, normally at 30° C. to 100° C. After mixing, the resultant mixture is cooled and then the salt is isolated by filtration or the like. Further, the mixing ratio of the starting compounds is not limited; however, a mixing molar ratio of fumaric acid to the quinoline derivative may range between 10.1 and 0.5:1. A molar ratio of fumaric acid to the quinoline derivative in the salt thus produced is also between 1:2 and 3:1.

Furthermore, these quinoline derivative components contain optically active compounds since they have asymmetric carbon atoms. Therefore, the optically active fumarates are included in the scope of the present invention. Further, in order to produce an optically active quinoline derivative, for example, optically active epichlorohydrin instead of racemic epichlorohydrin is used as a starting material according to a method, for example, one described in European Patent Publication No. 0363212 A2, or racemic quinoline derivatives can be optically resolved by a known method.

One or more of the quinoline derivative fumarates the present invention can be administered to a patient either simultaneously with a carcinostatic or after or before administration of the carcinostatic. They can be also administered to a patient separately from the carsinostatic. Therefore, a pharmaceutical composition including the quinoline derivative fumarate(s) of the present invention but not a carcinostatic can be prepared in the form suitable for the desired manner of administration and administered simlutaneously with or separately from the carcinostatic. A pharmaceutical composition including both the quinoline derivative fumarate(s) of the present invention and a carcinostatic can be also prepared in the form suitable for the desired manner of the administration and administered for the their simultaneous administration.

The dosage of the quinoline derivative fumarate(s) of the present invention to a patient varies depending on the symptom to be treated, the characteristics of the carcinostatic used with the fumarate(s) etc. Their daily dosage may generally range from 10 mg to 2000 mg per an adult. The daily dosage may be administered at once or divided into two or more times.

The quinoline derivative fumarates of the present invention may be administered orally in the form of an oral preparation such as tablets, garnules, powders, suspensions, capsules, syrups or the like. They may be also administered parenterally in the form of a parenteral preparation such as injections, suppositories, isotonic solutions for transfusion or the like. The tables can be formed, for example, by a conventional method using adsorbents such as crystalline cellulose, light silicic anhydrides or the like and excipients such as corn starch, lactose, calcium phosphate, magnesium stearate or the like. Aqueous suspensions, emulsions and aqueous solutions of the quinoline derivative fumarates of the present invention can be used as injections. The aqueous suspension can be prepared by a conventional method using cotton seed oil, corn oil, arachis oil, olive oil or the like. The emulsinons can be prepared by a conventional method using surface-active agents. The separate administration of carcinostatics may be carried out according to a conventional method suitable for each carcinostatic.

The present invention will be illustrated in detail by the following examples; however, the invention is not intended to be limited to these examples.

EXAMPLE 1

(a) 83 g of 5-hydroxyquinoline were dissolved in 1.5 l of dried dimethylformamide (DMF), and, after adding 23.3 g of sodium hydride (content: 60% ), the resulting mixture was stirred with heating at 50° C. for 30 minutes. 160 g of epichlorohydrin were added to the reaction mixture, and, after stirring with heating at 90° C. for 3 hours, the solvent was evaporated off under reduced pressure. Water was added to the resulting residue and extracted with chloroform. The chloroform extract was decolorized and purified with active carbon, dried with anhydrous mirabilite and then evaporated. The residue was purified by column chromatography on silica gel. 71 g of the targeted 5-(2,3-epoxypropoxy)quinoline were obtained as an oily substance by chromatography using a solvent mixture of chloroform:methanol=100:1 (volume ratio)for elution.

(b) 71 g of the above-mentioned 5-(2,3-epoxypropoxy) quinoline and 94 g of N-(2,2-diphenylacetyl)-piperazine were dissolved in 1.5 l of ethanol and then the resulting solution was refluxed with heating for 3 hours. After the reaction, ethanol was evaporated and the residue was purified by chromatography. The elution was carried out with a solvent miture of chloroform:methanol=50:1 (volume ratio) and the targeted fraction was concentrated under reduced pressure to obtain 101 g of 5-[3-{4-(2,2diphenylacetyl)piperazin-1-yl}-2- hydroxypropoxy]quinoline (compound No. 1).

Melting point: 162°–164° C.

(c) 100 g of the above-mentioned compound No. 1 were dissolved in 1 l of methanol and mixed with a solution obtained by dissoliving 74 g of fumaric acid in 500 ml of methanol. The mixture was heated to 40° C. and then allowed to stand at 0° C. overnight. The educed crystals were filtered and dried to obtain 91 g of the targeted 5-[3-{4-(2,2-diphenylacetyl)piperazin-1-yl}-2-hydroxypropoxy]quinoline fumarate (compound No. 2). This compound contained 1.5 mole of fumaric acid per one mole of the quinoline derivative and has the following physical properties:

Melting point: 211°–213° C. (decomposed) NMR $\delta$ ppm (CD$_3$OD); 2.55(d. 2H); 2.75–2.85(m. 4H); 3.62–3.68(m. 2H); 3.72–3.80 (m. 4H); 4.14–4.25(m. 2H); 4.25–4.35(m. 1H); 5.47(s. 1H); 6.73(s. 1.5×2H); 7.03(d. 1H); 7.17–7.35(m. 10H); 7.48–7.72(m. 3H); 8.76(d. 1H); 8.80–8.85(m. 1H). 1R $\nu$ cm$^{-1}$(KBr): 3385; 1644; 1592; 1277; 1179; 1110; 799.

| | Analytical values for elements (%) | | |
|---|---|---|---|
| | Carbon | Hydrogen | Nitrogen |
| Calculated value | 65.94 | 5.68 | 6.40 |
| Measured value | 66.01 | 5.62 | 6.04 |

EXAMPLE 2

The reaction was carried out in the same manner as Example 1-(c), except that 1-, 1.5-, 2- and 3-moles of fumaric acid were used per one mole of the quinoline derivative, respectively. Analyses of the resultant fumarates exhibited the same physical properties as shown in Example 1-(c).

EXAMPLE 3

The reaction was carried out in the same manner as Example 1-(c), except that ethanol was used in the place of methanol, and 73 g of fumarate were obtained. The physical properties of this compound were the same as shown in Example 1-(c).

EXAMPLE 4

4.0 g of S(−)5-[3-{4-(2,2-diphenylacetyl)-piperazin-1-yl}-2-hydroxypropoxy]quinoline, which were obtained by the same reaction as Example 1, except that R(−) epichlorohydrin was used as epichlorohydrin, were dissolved in 44 ml of ethyl acetate at room temperature and a solution obtained by dissolving 1.86 g of fumatic acid in 32 ml of methanol was added dropwise thereto. The solution was allowed to stand at room temperature overnight and then educed crystals were filtered and washed with 10 ml of a solvent miture (ethyl acetate:methanol=1:1 in the volume ratio). The crystals were dried to obtain 4.27 g of the targeted compound, S(−)5-[3-{4-(2,2-diphenylacetyl)piperazin-1-yl}-2-hydroxypropoxy] quinoline fumarate.

Melting point: 187°-189° C.

|  | Analytical values for elements (%) | | |
| --- | --- | --- | --- |
|  | Carbon | Hydrogen | Nitrogen |
| Calculated value | 65.94 | 5.69 | 6.41 |
| Measured value | 65.77 | 5.63 | 6.06 |

EXAMPLE 5

3.4 g of R(+)5-[3-{4-(2,2-diphenylacetyl) piperazin-1-yl}-2-hydroxypropoxy]quinoline, which were obtained by the same reaction as Example 1, except that S(+) epichlorohydrin was used as epichlorohydrin, were dissolved in 37 ml of ethyl acetate at room temperature and a solution obtained by dissolving 1.58 g of fumaric acid in 27 ml of methanol was added dropwise thereto. The solution was allowed to stand at room temperature overnight and then educed crystals were filtered and washed with 10 ml of a solvent mixture (ethyl acetate:methanol=1:1 in the volume ratio). The crystals were dried to obtain 3.56 g of the targeted compound, R(+)5-[3-{4-(2,2-diphenylacetyl)piperazin-1yl}-2-hydroxypropoxy]quinoline fumarate.

Melting point: 187°-189°C.

|  | Analytical values for elements (%) | | |
| --- | --- | --- | --- |
|  | Carbon | Hydrogen | Nitrogen |
| Calculated value | 65.94 | 5.69 | 6.41 |
| Measured value | 65.88 | 5.42 | 6.10 |

EXAMPLE 6

(a) 113 g of anhydrous piperazine were mixed with 800 ml of dioxane and 50 g of 5-chlorobenzosuberane were added. The resulting mixture was then refluxed with heating for 7 hours. After cooling, the insoluble substance was filtered and the solvent was evaporated under reduced pressure. A small amount of petroleum ether was added to the residue obtained by the evaporation and then the educed crystals were filtered and dried to obtain 51 g of targeted compound, N-(dibenzosuberan-5-yl)piperazine.

Melting point: 110°-111° C.

(b) 8.8 g of 5-(2,3-epoxypropoxy)quinoline obtained in Example 1-(a) and 12 g of N-(dibenzosuberan-5-yl)piperazine were dissolved in 200 ml of ethanol and then the resulting solution was refluxed with heating for 3 hours. After the reaction, the solvent was evaporated and the residue was purified by chromatography using a silica gel column. The elution was carried out with a solvent mixture of chloroform:methanol=50:1 (volume ratio) to obtain 14 g of the targeted compound, 5-[3-{4-(dibenzosuberan-5-yl)piperazin-1-yl}-2-hydroxypropoxy]quinoline (compound No. 3).

Melting point: 131°-133° C.

(c) 5 g of the above-mentioned quinoline derivative (compound No. 3) were dissolved in 200 ml of ethyl acetate and a solution obtained by dissolving 1.42 g of fumaric acid in 50 ml of methanol was added dropwise. 50 ml of ethyl acetate were additionally added thereto and the mixture was allowed to stand at room temperature overnight. The educed crystals were filtered, washed with ether and then dried to obtain 6.5 g of the targeted compound, 5-[3-{4-(dibenzosuberan-5-yl)piperazin-1-yl}-2-hydroxypropoxy]quinoline fumarate. This compound contained 1.5 moles of fumaric acid per one mole of the quiroline derivative and has the following physical properties.

Melting point: 139°141° C. (decomposed)

|  | Element analysis (%) | | |
| --- | --- | --- | --- |
|  | Carbon | Hydrogen | Nitrogen |
| Calculated value | 67.97 | 6.01 | 6.42 |
| Measured value | 67.63 | 6.01 | 6.27 |

2 g of 5-[3-{4-(2,2-diphenylacetyl)piperazin-1-yl}-2-hydroxypropoxy]quinoline were dissolved in 50 ml of methanol and the resulting solution was mixed with a solution obtained by dissolving 1.44 g of maleic acid in 10 ml of methanol. The mixed solution thus obtained was concentrated under reduced pressure to about one half the volume and then allowed to stand overnight. The reduced crystals were filtered and dried to obtain 2.3 g of the targeted compound No. 4, 5-[3-{4-(2,2-diphenylacetyl)piperazin-1-yl)-2-hydroxypropoxy]-quinoline malate. This compound contains 2 mols of maleic acid per one mole of the quinoline derivative and showed the following physical properties.

Melting point: 140°-142° C.

|  | Element analysis (%) | | |
| --- | --- | --- | --- |
|  | Carbon | Hydrogen | Nitrogen |
| Calculated value | 63.95 | 5.51 | 5.89 |
| Measured value | 63.51 | 5.64 | 5.67 |

Test Example 1

Solubility in water was measured according to the Pharmacopoeia Japan.

The compound No. 2 of Example 1-(c): 1.4 mg/ml

The compound No. 1 of Example 1-(b): less than 1 mg/ml

Test Example 2

Oral absorbability

Male beagles for experimental use were fasted one night before the administration of the test drugs. The drugs were suspended in a 0.1% TWEEN 80—0.1M NaCl—50 mM phosphate buffer solution for administration. All the drugs were forcefully administered in an amount of 50 mg/kg using an oral probe for dogs. Three animals were used for each test group. Blood samples were taken 9 times; 0.25, 0.5, 1, 1.5, 2, 4, 6, 9 and 24 hours after the administration. Blood samples of 5 ml were taken at each sampling time using a heparin-treated disposable injection syringe. Each blood was centrifuged at 3000 rpm for 15 minutes to obtain plasma. Drug concentrations in plasma were measured using HPLC and then calculated from a calibration curve for a standard sample. Results are shown in the following Tables.

TABLE 1

Concentration of the compound No. 1 of Example 1-(b) in plasma

| Sampling (hr) | Average (microgram/ml) | Standard deviation |
|---|---|---|
| 0.25 | 2.46 | 3.99 |
| 0.5 | 3.37 | 5.33 |
| 1 | 4.53 | 5.39 |
| 1.5 | 4.35 | 5.05 |
| 2 | 4.18 | 4.91 |
| 4 | 2.43 | 2.79 |
| 6 | 1.62 | 1.80 |
| 9 | 0.44 | 0.58 |

TABLE 2

Concentration of the compound No. 2 of Example 1-(c) in plasma

| Sampling (hr) | Average (microgram/ml) | Standard deviation |
|---|---|---|
| 0.25 | — | — |
| 0.5 | 14.68 | 4.42 |
| 1 | 13.21 | 5.50 |
| 1.5 | 12.72 | 4.12 |
| 2 | 10.51 | 2.55 |
| 4 | 6.76 | 0.45 |
| 6 | 3.70 | 0.32 |
| 9 | 1.21 | 0.16 |
| 24 | 0.03 | 0.05 |

Test Example 3

Oral absorbability test

7-Week-old female $CDF_1$ mice were fasted one night before the administration of the test drugs. The drugs were suspended in an aqueous 0.1% TWEEN 80 solution for administration and were forcefully administered in an amount of 100 mg/kg (for the compound No. 2 of Example 1-(c)) and 109 mg/kg (for the compound No. 4 of Comparative Example 1) so as to get the equivalent molarity using a probe for oral administration. Three animals were used for each test group. Blood samples were taken 4 times; 0.5, 1.0, 2.0 and 4.0 hours after the administration. Blood samples were taken by cardiocentesis under anesthesia with chloroform using a heparin-treated disposable injection syringe, Each blood was centrifuged at 4° C. at 6000 rpm for 10 minutes to obtain plasma. Drug concentrations in plasma were measured using HPLC and then calculated from a calibration curve for a standard sample, Results are shown in the following Tables.

TABLE 3

Concentration of the compound No. 2 of Example 1-(c) in plasma

| Sampling (hr) | Average of 3 mice (microgram/ml) | Standard deviation |
|---|---|---|
| 0.5 | 17.98 | 3.47 |
| 1.0 | 21.82 | 0.11 |
| 2.0 | 16.05 | 1.90 |
| 4.0 | 13.68 | 1.78 |

TABLE 4

Concentration of the compound No. 4 of Comparative Example 1 in plasma

| Sampling (hr.) | Average of 3 mice (microgram/ml) | Standard deviation |
|---|---|---|
| 0.5 | 14.30 | 2.68 |
| 1.0 | 11.36 | 2.62 |
| 2.0 | 11.93 | 0.96 |
| 4.0 | 5.99 | 3.67 |

Test Example 4

Carcinostatic-effect-stimulating activity

Vincristine-resistant mouse leukemia cells, P388/VCR, were suspended at a concentration of $2 \times 10^4$ cells/ml in an RPMI-1640 medium solution containing 85% fetal calf serum. 2 ml of the cancer cell suspension per tube (12×75 mm) were inoculated and incubated at 37° C. in a 5% $CO_2$ atmosphere. After 6 hours, vincristine and the compound No. 2 of Example 1-(c) at a concentration of 0.3, 1 or 3 microgram/ml and the incubation was continued at 37° C. under a 5% $CO_2$ atmosphere for 72 hours. The cell culture was added to 9.5 ml of ISOTON II, the number of cells was counted using a call counter and then 50% growth inhibiting concentrations of vincristine $IC_{50}$ (ng/ml) were calculated. Results are shown in Table 5

TABLE 5

| Compound | $IC_{50}$ of vincristine (ng/ml) Concentration of compound (microgram/ml) | | | |
|---|---|---|---|---|
| | 0 | 0.3 | 1 | 3 |
| No. 2 of Example 1-(c) | 142 | 56.9 | 22.0 | 4.12 |

What is claimed is:

1. A fumarate of a quinoline compound of the following formula (1):

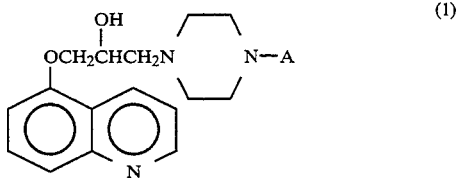

in which A represents the following formula (2) or formula (3):

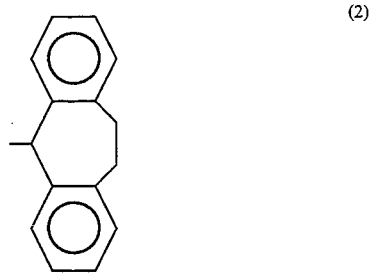

in which $R_1$, $R_2$ and $R_3$ represent independently a hydrogen atom or a phenyl group.

2. A fumarate of an optically active quinoline compound of the following formula (4):

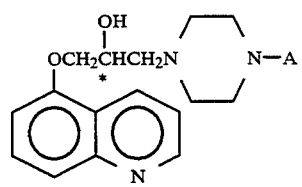

wherein A represents a group of the following formula (2) or (3):

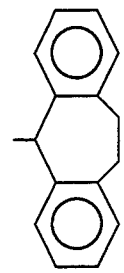

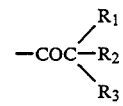

in which $R_1$, $R_2$ and $R_3$ represent independently a hydrogen atom or a phenyl group; and * represents an asymmetrical carbon atom.

3. A fumarate as claimed in claim 2, wherein the quinoline derivative has a (+) or (−) form.

4. A pharmaceutical composition for stimulation of a carcinostatic effect comprising an effective amount of the fumarate of claim 1, 2 or 3 and a carrier or diluent.

5. A method of stimulating a carcinostatic effect comprising the step of administering the fumarate of claim 1, 2 or 3 to a patient treated with a carcinostatic.

* * * * *